(12) United States Patent
Pettibon

(10) Patent No.: US 6,517,506 B1
(45) Date of Patent: Feb. 11, 2003

(54) CERVICAL TRACTION DEVICE AND METHOD

(76) Inventor: Burl Pettibon, 89 Rift Island Dr., Gig Harbor, WA (US) 98335

(*) Notice: Subject to any disclaimer, the term of this patent is extended or adjusted under 35 U.S.C. 154(b) by 0 days.

(21) Appl. No.: 09/972,590

(22) Filed: Oct. 5, 2001

Related U.S. Application Data

(63) Continuation-in-part of application No. 09/960,834, filed on Sep. 21, 2001, which is a continuation-in-part of application No. 09/833,395, filed on Apr. 11, 2001.

(51) Int. Cl.[7] .................................................. A61F 5/00
(52) U.S. Cl. ........................................... 602/32; 602/36
(58) Field of Search .............................. 602/16, 17, 18, 602/32–40

(56) References Cited

U.S. PATENT DOCUMENTS

| | | | | | |
|---|---|---|---|---|---|
| 2,633,125 A | * | 3/1953 | Yellin | ........................ | 602/32 |
| 2,658,506 A | * | 11/1953 | Haskell | ........................ | 602/32 |
| 2,701,564 A | * | 2/1955 | Wilhelm | ........................ | 602/32 |
| 2,808,049 A | * | 10/1957 | Graham | ........................ | 602/32 |

* cited by examiner

*Primary Examiner*—Michael A. Brown
(74) *Attorney, Agent, or Firm*—Seed IP Law Group LLC

(57) ABSTRACT

A traction device is provided that includes a harness coupled to a suspension assembly for suspending the harness at a predetermined height. The harness includes a neck support placed behind a user's neck and a chin rest connected to the neck support on which the user's chin rests. Hand grips extending from the chin or forehead rest allow a user to manually grasp the chin rest and support a portion of their weight as the remainder of their weight is supported by the cervical spine through the traction device. Approximately six to eight repetitions of the method, each performed for ten to twenty seconds, result in nourishment, repair, and regeneration of avascular tissues in the disks, ligaments, cartilage, and improved cervical and lumbar lordotic curves.

27 Claims, 3 Drawing Sheets

CERVICAL TRACTION DEVICE AND METHOD

CROSS-REFERENCE TO RELATED APPLICATION

This application is a continuation-in-part of a U.S. patent application Ser. No. 09/960,834, filed on Sep. 21, 2001, which is a continuation-in-part of U.S. patent application Ser. No. 09/833,395, filed Apr. 11, 2001, which applications are incorporated herein by reference in their entirety.

BACKGROUND OF THE INVENTION

1. Technical Field

The present invention pertains to traction devices, and, more particularly, to a cervical traction device and method of using the same to improve the cervical and lumbar lordotic curves.

2. Description of the Related Art

By the time a person reaches twelve years of age, their disks, ligaments, and cartilage no longer have direct blood supply for nourishment and elimination of tissue cell wastes. These tissues are then referred to as "avascular" tissues. Avascular tissues require nourishment and waste elimination to function normally, to repair and regenerate as when they were vascular. In order to nourish, repair, and regenerate avascular tissue, motion is now required to pump the nourishing fluids in and the waste produce out.

The required motion necessary for avascular tissue health can be prevented due to injury. The first reaction to an injury of the body is splinting by the related muscles to protect the injured part. Splinting prevents the voluntary motion necessary for nourishment, waste elimination, repair, and healing of the injury.

Experiments have been performed to determine the best treatment for repair and healing avascular tissue, such as spinal disks and ligaments. It was determined that immobility was harmful to the healing of mobile tissues, and that passive motion causes healing. Moreover, it has been found that chondrogenesis of bone and cartilage was produced by intermittent compression and traction.

Moreover, it has been found that loading and unloading cycles initiated by traction and compression of the spine to achieve cyclical long access loading and unloading of the injured disks of the spine cause a remarkable "self-healing" time. It has also been found by a number of tests that degenerated disks are actually stronger than normal disks when subjected to compressive loading and traction unloading cycles.

Hence, there is a need for repetitive loading and unloading of the skeletal system to aid in the recovery from injuries and the correction of neck and low back problems to improve posture and reduce pain.

SUMMARY OF THE INVENTION

The disclosed embodiments of the present invention are directed to a cervical traction device and method. The device includes a harness forming an enclosed loop having a rigid portion and a flexible portion sized and shaped to be fit around the user's neck with the rigid portion under the user's chin and the flexible portion around the back of the user's neck; and a suspension assembly attached to the harness and configured to suspend the harness at a selectable height.

In accordance with the foregoing embodiment, the loop preferably has an adjustable diameter, and the rigid portion is configured to enable manual grasping by the user. The suspension assembly has an adjustable length and includes an elongate filament attached at one end to the harness and at the other end to an attachment device for suspending the harness from existing structural supports.

In accordance with another embodiment of the invention, a cervical traction device is provided that includes a harness comprising a chin rest and a neck support and a suspension assembly for suspending the harness at a selected height.

In accordance with another aspect of the foregoing embodiment, the chin rest comprises a bar formed of rigid material and the neck support comprises a flexible strap having first and second ends attached to the chin rest, with one of the first and second ends removably attached thereto. Ideally, hand grips are formed on the bar to project beyond the attachment points of the neck support to enable manual grasping of the chin rest by the user. Preferably, tubular foam pads are placed over the chin rest and neck support to cushion the user's chin and neck, respectively.

In accordance with yet a further aspect of the foregoing embodiment, the suspension assembly includes a suspender that, in one embodiment, is formed from a flexible filament, such as a rope. In addition, the suspension assembly includes an attachment device formed at one end of the suspender, such as a hook that is sized and shaped to be placed over the top of a door. Ideally, the suspender has an adjustable length to enable the user to adjust the height of the harness such that the hand grips are even with the user's should height.

In accordance with a further embodiment of the present invention, a cervical traction device for use with an existing structural support is provided that includes an elongate rigid bar; a flexible band having first and second ends attached to the bar to form a loop sized to fit around the user's neck with the bar under the user's chin and the band positioned around the back of the user's neck; an elongate suspender having a first end attached to the bar and a second end; and an attachment device connected to the second end of the suspender and configured for attachment to the structural support.

In accordance with the foregoing embodiment, the rigid bar preferably extends beyond the band to form hand grips. In accordance with a method for use with the foregoing devices of the present invention, the harness or loop is suspended at a selected height; the harness is placed around the user's neck such that the chin rest is under the chin and the loop or band extends around the back of the user's neck; the chin rest is manually grasped at hand grips formed thereon; and the user's weight is progressively supported by the harness. The chin rest may also function as a head rest.

In accordance with the foregoing method of the present invention, ideally the harness and chin bar are suspended to be even with the user's shoulders, and the hand grips are grasped with the user's palms toward the face. Ideally, a repetition period in the range of one to twenty seconds is accomplished where the user's weight is partially supported by the harness, and the number of repetitions are in the range of six to sixty.

In accordance with yet a further embodiment of the invention, the harness is placed around the user's neck and a padded forehead rest is placed against the user's forehead. The forehead rest has handgrips that are manually grasped by the user, and the user's weight is progressively supported by the harness.

As will be readily appreciated from the foregoing, repetitive traction using the device described above will produce loading and unloading cycles which aid in nourishing, repairing, and regenerating avascular tissue. It will also aid in the correction of neck and low back problems because of the effect it has on cervical spine lordosis and lateral spine angle deviations that cause impedance on the perimeter cord tracts that connect the brain, low back and legs. Furthermore, it is difficult to correct number two and number three cervicothoracic spinal posture configuration unless repetitive traction is performed first so that the visco-elastic properties of spinal discs and ligaments are lowered so that the addition of spinal adjusting followed by head, shoulder, and hip weighting procedures can be effective.

BRIEF DESCRIPTION OF THE DRAWINGS

The following detailed description of the device and method of the present invention will be more readily appreciated as the same become better understood from the accompanying drawings, wherein.

DETAILED DESCRIPTION OF THE INVENTION

Figure 1:
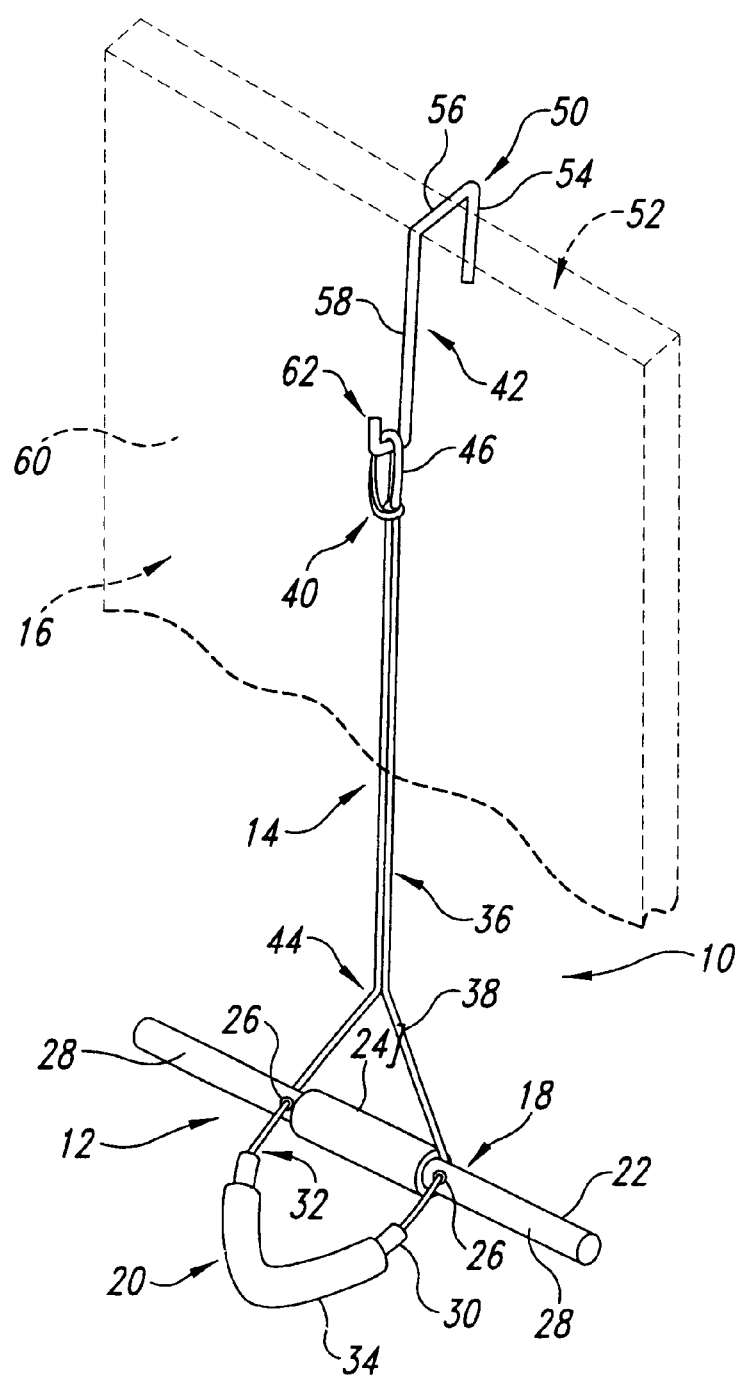
FIG. 1 is an isometric projection of the cervical traction device formed in accordance with the present invention.

Referring initially to FIG. 1, shown therein is one embodiment of a cervical traction device 10 formed in accordance with the present invention. The device 10 includes a harness 12 attached to a suspension assembly 14. The device 10 is shown suspended from a door 16 (shown in Phantom).

In the embodiment shown in FIG. 1, the harness 12 comprises a chin rest 18 and a neck support 20 attached thereto. The chin rest 18 is formed from an elongate, rigid bar in the form of a tube 22 having a sleeve 24 centrally disposed thereon. The tube 22 may be formed of plastic, wood, metal, or other suitable material that is rigid and generally inflexible. The sleeve 24 is slidably received over the tube 22, and the sleeve 24 is preferably formed of cushioned material, such as foam to protect the chin of a user when in use. A pair of openings 26 are formed transversely through the tube 22 and are spaced equally distant from the sleeve 24 such that when the tube 22 is attached to the suspension assembly 14, the tube 22 will be suspended in a substantially horizontal orientation. The portion of the tube 22 projecting out from the sleeve 24 forms hand grips 28 to enable manual grasping of the tube 22 by a user.

The neck support 20 is, in this embodiment, formed from a substantially U-shaped tube 30 having a longitudinal axial bore 32 formed therein. A padded sleeve 34 is slidably received over the U-shaped tube 30 for cushioning the back of the user's neck when in use. Ideally, the sleeve is formed of foam material, the same is used for the sleeve 24 on the chin rest 18. It is to be understood that the neck support 20 may have a different construction to accomplish the same purpose, such as a strap or wide belt having both of its ends connected to the tube 22.

The suspension assembly 14 includes an elongate suspender 36, preferably formed of a flexible filament, such as rope or other similar material. In the embodiment shown in FIG. 1, the suspender 36 is a rope 38 that has an attachment end 40 connected to an attachment member 42 and a suspended end 44 coupled to the harness 12. More particularly, the rope 38 is threaded through the openings 26 and the tube 22 and through the axial bore 32 of the chin rest 18 such that the tube 22 can slide freely along the suspended end 44 of the suspender 36. The ends of the rope 38 are attached together to form an attachment ring 46 for connection to the attachment member 42. In this manner, the chin rest 18 and neck support 20 form an enclosed loop that is adjustable in its diameter by sliding the tube 22 along the attachment end 40 of the suspender 36.

The attachment member 42 in this embodiment comprises a U-shaped hook 50 configured for placement over the top 52 of the door 16. More particularly, the hook 50 has a first leg 54 connected to a transverse member 56 that bears on the top of the door 52. A second leg 58 depends downward from the transverse member 56 along a vertical face 60 as a brace for the attachment member 42. A hook 62 is formed at the end of the second leg 58 where the attachment ring 46 is placed.

Various methods may be used for changing the length of the suspender 36, such as tying knots in the rope 38 or changing the size of the attachment ring 46 formed by the rope. It is to be understood that buckles or other hardware may also be used with the rope 38 for adjusting its length. In addition, it is to be understood that other materials than rope may be used for the suspender 36 without departing from the spirit and scope of the invention.

Figure 2:
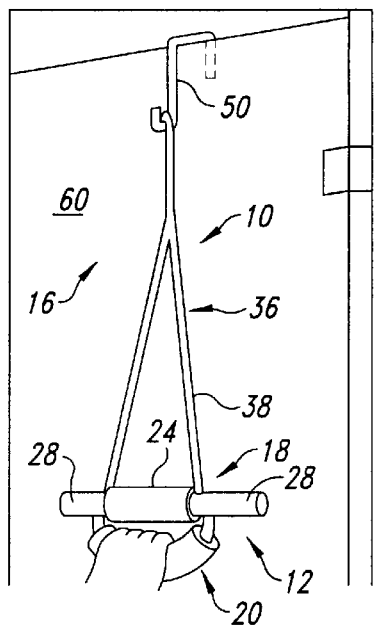
FIG. 2 is an isometric projection of a first step of a method in accordance with the present invention.
Figure 3:
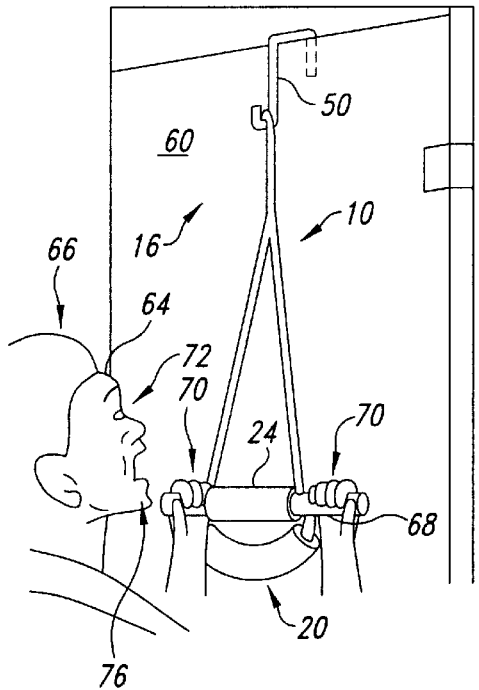
FIG. 3 is an isometric projection of a second step in accordance with the method of the present invention.
Figure 4:
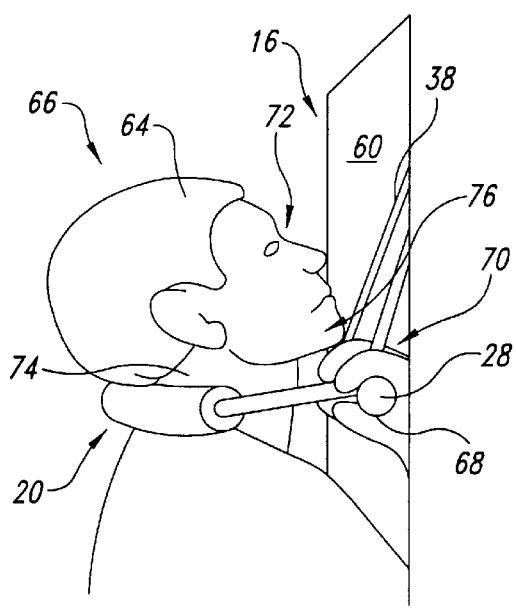
FIG. 4 is an isometric projection of a further step of the method in accordance with the present invention.

The method of using the cervical traction device 10 will now be described in conjunction with FIGS. 2–4. Referring initially to FIG. 2, the device 10 is first attached to the door 16 by placing the hook 50 over the top 52 of the door 16, preferably about eight to twelve inches from the hinged side of the door. The rope 38 is then looped over the hook 62 and the length of the rope 38 is adjusted to be the patient's height. Ideally, the harness 12 is suspended such that the tube 22 is as substantially the same height as the user's shoulders. Alternatively, the neck support 20 should hang just slightly lower than the head 64 of a user 66. It is important to note that the hook 50 should not be used on a door that is too wide for the hook. Rather, it is important that the hook fit properly over both sides of the door 16.

To train a patient, the tube 22 is slid down the rope 38 until it contacts the neck support 20. At this point, the hand grips 28 should be about shoulder height. The user 66 places their elbows and knees against the vertical face 60 of the door 16. The user's feet should be shoulder width apart.

The user then manually grasps the hand grips 28, ideally with the palms 68 of the hands 70 towards the user's face 72. While holding the hand grips 28 firmly, the user breathes in as deep as possible and relaxes the user's knees so that a portion of the user's body weight is supported by the device 10. Some pulling in the low back should be felt by the user. Traction amount and repetitions are controlled by bending and straightening of the user's knees.

The user practices using the device 10 in accordance with the foregoing until they are comfortable with the device and they are assured the device is functioning properly. To begin actual use, the neck support 20 is placed behind the user's neck 74 and the user's chin 76 rests on the chin rest 18, as shown in FIG. 4. The user 66 should then place one hand 70 on each hand grip 28 with the palms 68 towards the user's face 72. The user 66 then inhales as deep as possible and relaxes their knees so that approximately 90% of the user's weight is supported by the arms and the cervical spine is supporting 10% of the user's weight through the traction device 10 completely exhale before the next leading cycle. It is important to note that placing too much weight on the cervical spine can cause muscle splinting and no traction will result in the neck, mid back, and low back.

Ideally, a single repetition period of the foregoing involves the user supporting a portion of their weight on the traction device 10 for a period of time ranging from one second to twenty seconds, and ideally for a slow count of ten, which is approximately twenty seconds. Use of the traction should be started with six to eight repetitions the first day and increasing to thirty repetitions, and eventually increasing to sixty repetitions within 14 days.

Some discomfort is expected where the device contacts the neck and chin in the beginning. If pain is experienced in the neck after use, ice should be used on the neck followed by a period of rest before using the traction device 10 again. Subsequent use should be for shorter periods of time and with less weight on the traction device until pain is no longer experienced.

Figure 5:
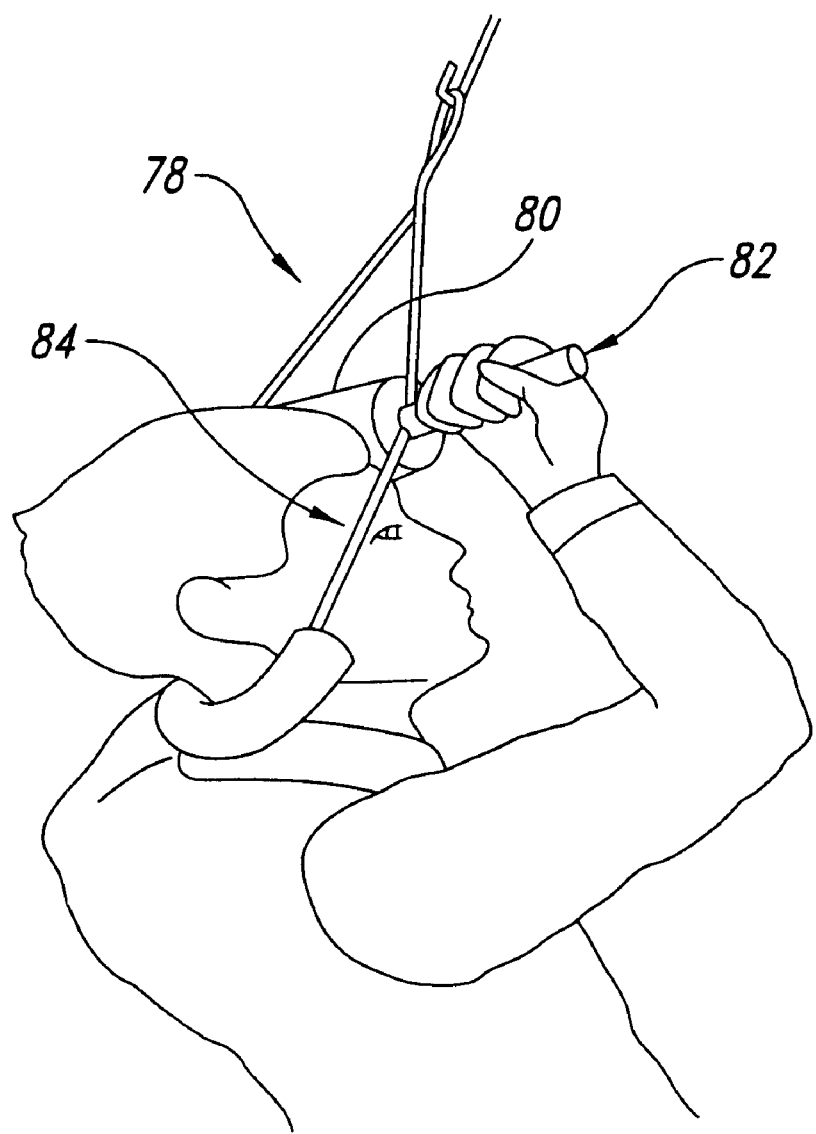
FIG. 5 is an isometric projection of an alternative method of use in accordance with another embodiment of the invention.

While a preferred embodiment of the invention has been illustrated and described, it is to be understood that various changes may be made therein without departing from the spirit and scope of the invention. For example, as shown in FIG. 5, a TMJ diagnosed patient would use a modified device 78, wherein a sleeve 80 having larger diameter padding is formed around the tube 82 to form a forehead rest that is placed over the user's forehead 84 instead of under the chin. The TMJ will therefore not be aggravated when the device 78 is used as described above. Hence, the invention is to be limited only by the scope of the claims that follow and the equivalence thereof.

The embodiments of the invention in which an exclusive property or privilege is claimed are defined as follows:

1. A cervical traction device, comprising:
    a harness comprising an enclosed loop having a rigid portion and a flexible portion, the loop sized and shaped to fit around a user's neck with the rigid portion under the user's chin and the flexible portion around the back of the user's neck; and
    a suspension assembly attached to the rigid portion on the harness and configured to suspend the harness at a selectable height to urge the neck into a lordotic curved position.

2. The device of claim 1, wherein the loop has an adjustable diameter.

3. The device of claim 1, wherein the rigid portion is configured to enable manual grasping by the user.

4. The device of claim 1, wherein the suspension assembly comprises an elongate suspender that has an adjustable length.

5. The device of claim 4, wherein the suspension assembly further comprises an attachment device for attaching the suspension assembly to existing structural supports.

6. A cervical traction device, comprising:
    a harness, the harness comprising a chin rest and a neck support connected to the chin rest and configured to be placed around a user's neck, the chin rest comprising a rigid chin rest member, and the neck support comprising a flexible filament having first and second ends attached to the chin rest; and
    a suspension assembly attached to the chin rest for suspending the harness at a predetermined height to urge the neck into a lordotic curved position.

7. The device of claim 6, wherein the chin rest comprises a rigid bar, and the neck support comprises a strap having first and second ends attached to the chin rest.

8. The device of claim 7, wherein at least one of the first and second ends of the neck support are removably attachable to the chin rest.

9. The device of claim 7, further comprising hand grips formed on the chin rest that are sized and shaped to enable manual grasping by a user.

10. The device of claim 7, wherein the suspension assembly further comprises an elongate suspender having a first end attached to the harness and a second end attached to an attachment device.

11. The device of claim 10, wherein the suspender comprises a bendable filament.

12. The device of claim 11, wherein the suspender has an adjustable length.

13. The device of claim 11, wherein the attachment device comprises a hook member sized and shaped to be placed over the top of a door.

14. A cervical traction device for use with an existing structural support, the device comprising:
    a rigid bar;
    a flexible band having first and second ends attached to the bar to form a loop sized to fit around a user's neck with the bar under the user's chin and the band positioned around the back of the user's neck;
    an elongate suspender having a first end attached to the bar and a second end; and
    an attachment device connected to the second end of the suspender and configured for attachment to the structural support to urge a user's neck into a lordotic curved position.

15. The device of claim 14, wherein the rigid bar extends beyond the flexible band to form first and second hand grips.

16. The device of claim 14, wherein the suspender comprises a rope.

17. The device of claim 14, wherein the attachment device comprises a hook sized and shaped to be placed over a door.

18. A cervical traction method for use with a cervical traction device having a harness that includes a chin rest with hand grips and a neck support having first and second ends attached thereto to form a loop and a suspender having one end attached to the harness and a second end attached to an attachment device configured for attachment to a structural support, the method comprising:
    suspending the harness from a structural support at a predetermined height;
    placing the harness around the neck with the chin on top of the chin rest and the neck support placed around the back of the neck;
    manually grasping the hand grips; and
    relaxing the knees aggressively such that at least a portion of the body weight is supported by the harness.

19. The method of claim 18, wherein the harness is suspended at a height that the hand grips are at shoulder height.

20. The method of claim 18, wherein the weight is supported on the harness for a repetition period in the range of one to twenty seconds with the number of repetitions ranging from six to sixty.

21. A cervical traction method for use with a cervical traction device having a harness that includes a head rest with hand grips and a neck support having first and second ends attached thereto to form a loop and a suspender having one end attached to the harness and a second end attached to an attachment device configured for attachment to a structural support, the method comprising:
    suspending the harness from a structural support at a predetermined height;

placing the harness around the neck with the forehead rest against the forehead and the neck support placed around the back of the neck;

manually grasping the hand grips; and relaxing the knees aggressively such that at least a portion of the body weight is supported by the harness.

22. The method of claim 18, wherein the harness is suspended at a height that the hand grips are at the user's forehead height.

23. The method of claim 18, wherein the weight is supported on the harness for a repetition period in the range of one to twenty seconds with the number of repetitions ranging from six to sixty.

24. A cervical traction device, comprising:

a harness comprising a chin rest and a neck support connected to the chin rest and configured to be placed around a user's neck, the chin rest comprising a rigid bar, and the neck support comprising a strap having first and second ends attached to the chin rest; and a suspension assembly for suspending the harness at a predetermined height.

25. A cervical traction device, comprising:

a harness comprising a chin rest and a neck support connected to the chin rest and configured to be placed around a user's neck, the chin rest comprising a rigid bar, and the neck support comprising a strap having first and second ends attached to the chin rest, at least one of the first and second ends of the neck support configured to be removably attachable to the chin rest; and a suspension assembly for suspending the harness at a predetermined height.

26. A cervical traction device, comprising:

a harness comprising a chin rest and a neck support connected to the chin rest and configured to be placed around a user's neck, the chin rest comprising a rigid bar, and the neck support comprising a strap having first and second ends attached to the chin rest;

a suspension assembly for suspending the harness at a predetermined height; and hand grips formed on the chin rest, the hand grips sized and shaped to enable manual grasping of the chin rest by a user.

27. A cervical traction device, comprising:

a harness comprising a chin rest and a neck support connected to the chin rest and configured to be placed around a user's neck, the chin rest comprising a rigid bar, and the neck support comprising a strap having first and second ends attached to the chin rest; and a suspension assembly for suspending the harness at a predetermined height, the suspension assembly further comprising an elongate suspender having a first end attached to the harness and a second end attached to an attachment device.

* * * * *